(12) United States Patent
Macaulay et al.

(10) Patent No.: US 8,214,015 B2
(45) Date of Patent: Jul. 3, 2012

(54) IN VIVO LOCALIZATION AND TRACKING OF TISSUE PENETRATING CATHETERS USING MAGNETIC RESONANCE IMAGING

(75) Inventors: Patrick Macaulay, Windsor, CA (US); Asha Nayak, Menlo Park, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1846 days.

(21) Appl. No.: 11/279,773

(22) Filed: Apr. 14, 2006

(65) Prior Publication Data

US 2006/0184011 A1 Aug. 17, 2006

Related U.S. Application Data

(63) Continuation-in-part of application No. 10/467,274, filed as application No. PCT/US02/03941 on Feb. 6, 2002, now Pat. No. 7,966,057.

(60) Provisional application No. 60/266,800, filed on Feb. 6, 2001.

(51) Int. Cl.
*A61M 25/00* (2006.01)

(52) U.S. Cl. .......... 600/424; 606/130; 604/528

(58) Field of Classification Search .......... 600/407–435; 606/130, 159, 167; 604/527–529
See application file for complete search history.

(56) References Cited

U.S. PATENT DOCUMENTS

| | | |
|---|---|---|
| 5,217,400 A | 6/1993 | Creek et al. |
| 5,307,808 A | 5/1994 | Dumoulin et al. |
| 5,343,865 A | 9/1994 | Gardineer et al. |
| 5,425,370 A | 6/1995 | Vilkomerson |
| 5,465,717 A | 11/1995 | Imran et al. |
| 5,542,915 A | 8/1996 | Edwards et al. |
| 5,558,073 A | 9/1996 | Pomeranz et al. |
| 5,568,809 A | 10/1996 | Ben-haim |
| 5,578,007 A | 11/1996 | Imran |
| 5,647,361 A | 7/1997 | Damadian |
| 5,669,388 A | 9/1997 | Vilkomerson |
| 5,694,945 A | 12/1997 | Ben-haim |
| 5,713,946 A | 2/1998 | Ben-haim |
| 5,722,401 A | 3/1998 | Pietroski et al. |
| 5,729,129 A | 3/1998 | Acker |
| 5,730,128 A | 3/1998 | Pomeranz et al. |
| 5,752,513 A | 5/1998 | Acker et al. |

(Continued)

FOREIGN PATENT DOCUMENTS

WO WO02/062265 8/2002

(Continued)

OTHER PUBLICATIONS

Shinner, M. et al., The Diagnostic Accuracy of Ex Vivo MRI for Human Atherosclerotic Plaque Characterization; Arterioscler. Throm. Vasc. Biol. 19:2756-2761 (1999).

(Continued)

*Primary Examiner* — Sanjay Cattungal (57) ABSTRACT

Magnetic resonance image (MRI) guided tissue penetrating catheters and their methods of use. One or more MRI apparatus (e.g., one or more coils) are positioned on or in a catheter device that includes a tissue penetrator that may be used to form a penetration tract from a body lumen in which the catheter is positioned to a target location outside of that body lumen. The MRI apparatus (e.g., coil(s)) is/are used in conjunction with an MRI imaging system to indicate the position and/or rotational orientation of the penetrating catheter within the subject's body.

29 Claims, 3 Drawing Sheets

U.S. PATENT DOCUMENTS

| | | | |
|---|---|---|---|
| 5,820,568 A | 10/1998 | Willis | |
| 5,830,222 A * | 11/1998 | Makower | 606/159 |
| 5,833,608 A | 11/1998 | Acker | |
| 5,931,818 A | 8/1999 | Werp et al. | |
| 5,935,061 A | 8/1999 | Acker et al. | |
| 5,968,053 A * | 10/1999 | Revelas | 606/108 |
| 6,004,269 A | 12/1999 | Crowley et al. | |
| 6,015,414 A | 1/2000 | Werp et al. | |
| 6,068,638 A | 5/2000 | Makower | |
| 6,071,292 A | 6/2000 | Makower et al. | |
| 6,148,823 A | 11/2000 | Hastings | |
| 6,159,225 A | 12/2000 | Makower | |
| 6,171,240 B1 | 1/2001 | Young et al. | |
| 6,171,303 B1 * | 1/2001 | Ben-Haim et al. | 606/15 |
| 6,176,829 B1 | 1/2001 | Vilkomerson | |
| 6,190,353 B1 | 2/2001 | Makower et al. | |
| 6,198,962 B1 | 3/2001 | Su | |
| 6,233,474 B1 * | 5/2001 | Lemelson | 600/411 |
| 6,253,770 B1 * | 7/2001 | Acker et al. | 128/899 |
| 6,254,573 B1 * | 7/2001 | Haim et al. | 604/157 |
| 6,283,951 B1 | 9/2001 | Flaherty et al. | |
| 6,285,898 B1 * | 9/2001 | Ben-Haim | 600/374 |
| 6,302,875 B1 | 10/2001 | Makower et al. | 604/528 |
| 6,321,109 B2 * | 11/2001 | Ben-Haim et al. | 600/424 |
| 6,327,492 B1 * | 12/2001 | Lemelson | 600/434 |
| 6,332,088 B1 | 12/2001 | Zhang et al. | |
| 6,332,089 B1 | 12/2001 | Acker et al. | |
| 6,375,615 B1 | 4/2002 | Flaherty et al. | |
| 6,393,314 B1 | 5/2002 | Watkins et al. | |
| 6,400,980 B1 * | 6/2002 | Lemelson | 600/478 |
| 6,508,824 B1 * | 1/2003 | Flaherty et al. | 606/185 |
| 6,544,230 B1 | 4/2003 | Flaherty et al. | |
| 6,579,311 B1 | 6/2003 | Makower | |
| 6,591,129 B1 * | 7/2003 | Ben-Haim et al. | 600/424 |
| 6,592,526 B1 * | 7/2003 | Lenker | 600/463 |
| 6,602,241 B2 | 8/2003 | Makower et al. | |
| 6,655,386 B1 * | 12/2003 | Makower et al. | 128/898 |
| 6,660,024 B1 * | 12/2003 | Flaherty et al. | 600/439 |
| 6,685,648 B2 * | 2/2004 | Flaherty et al. | 600/464 |
| 6,702,777 B2 * | 3/2004 | Haim et al. | 604/66 |
| 6,709,444 B1 | 3/2004 | Makower | |
| 6,726,677 B1 | 4/2004 | Flaherty et al. | |
| 6,746,464 B1 | 6/2004 | Makower | |
| 6,751,492 B2 * | 6/2004 | Ben-Haim | 600/374 |
| 6,788,967 B2 * | 9/2004 | Ben-Haim et al. | 600/424 |
| 6,915,149 B2 * | 7/2005 | Ben-Haim | 600/374 |
| 7,306,593 B2 * | 12/2007 | Keidar et al. | 606/34 |
| 7,384,411 B1 * | 6/2008 | Condado | 604/96.01 |
| 2001/0003790 A1 * | 6/2001 | Ben-Haim et al. | 600/424 |
| 2002/0013615 A1 * | 1/2002 | Haim et al. | 607/120 |
| 2002/0045809 A1 * | 4/2002 | Ben-Haim | 600/374 |
| 2002/0165448 A1 * | 11/2002 | Ben-Haim et al. | 600/424 |
| 2003/0032936 A1 | 2/2003 | Lederman | |
| 2003/0125615 A1 * | 7/2003 | Schwartz | 600/374 |
| 2003/0129750 A1 * | 7/2003 | Schwartz | 435/377 |
| 2004/0059280 A1 | 3/2004 | Makower et al. | |
| 2004/0147837 A1 * | 7/2004 | Macaulay et al. | 600/424 |
| 2006/0079740 A1 * | 4/2006 | Silver et al. | 600/309 |
| 2009/0216125 A1 * | 8/2009 | Lenker | 600/445 |
| 2010/0210938 A1 * | 8/2010 | Verard et al. | 600/424 |

FOREIGN PATENT DOCUMENTS

| | | |
|---|---|---|
| WO | WO 02/062265 | 8/2002 |
| WO | WO 03/013641 | 2/2003 |
| WO | WO2004/068947 | 8/2004 |
| WO | WO 2005/112836 | 12/2005 |

OTHER PUBLICATIONS

Hatsukami, T.S., et al., Visualization of Fibrous Cap Thickness and Rupture in Human Atherosclerotic Carotid Plaque in Vivo With High-Resolution Magnetic Resonance Imaging. Circulation 102:959-964 (2000).

Serfaty, Jean-Michael et al., "Toward MRI-Guided Coronary Cathetrization : Visualization of Guiding Catheters, Guidewires and Anatomy in Real Time," J. Mag. Reson. Imaging, 12:590-594 (2003).

* cited by examiner

Fig. 2 C

IN VIVO LOCALIZATION AND TRACKING OF TISSUE PENETRATING CATHETERS USING MAGNETIC RESONANCE IMAGING

RELATED APPLICATION

This patent application is a continuation-in-part of copending U.S. patent application Ser. No. 10/467,274 entitled "Methods and Apparatus for Guided Transluminal Interventions Using Vessel Wall Penetrating Catheters and Other Apparatus" filed Aug. 5, 2003, which is national stage application of PCT/US02/03941 filed on Feb. 2, 2002, which claims priority to U.S. Provisional patent Application No. 60/266,800 filed on Feb. 6, 2001, the entire disclosure of each such related application being expressly incorporated herein by reference.

FIELD OF THE INVENTION

The present invention relates generally to methods and apparatus for medical treatment and more particularly to magnetic resonance image (MRI) guided tissue penetrating catheters and their methods of use.

BACKGROUND

High resolution MRI techniques have proven to be useable for assessing the anatomy of various blood vessels, including coronary blood vessels, as well as pathological lesions on blood vessel walls. see, Shinnar, M. et al., The Diagnostic Accuracy of Ex Vivo MRI for Human Atherosclerotic Plaque Characterization; Arterioscler. Thromb. Vasc. Biol. 19:2756-2761 (1999) and Hatsukami, T. S., et al., Visualization of Fibrous Cap Thickness and Rupture in Human Atherosclerotic Carotid Plaque In Vivo With High-Resolution Magnetic Resonance Imaging. Circulation 102:959-964 (2000). Also, because MRI is sensitive to changes in temperature, it can be used to assess temperature differences within the body or to monitor heat-based therapies.

The advent of rapid image acquisition sequences has rendered MRI useable as a means for guiding the in vivo positioning of guidewires, catheters and other interventional devices. For example, researchers have devised MRI guidable catheters and guidewires that incorporate MRI antennae and real-time visualization of a guidewire, guiding catheter, and anatomy has been accomplished. See, Serfaty, Jean-Michael, et al., Toward MRI-Guided Coronary Cathetrization: Visualization of Guiding Catheters, Guidewires and Anatomy in Real Time, J. Mag. Reson. Imaging, 12:590-594 (2003). Examples of MRI apparatus (e.g., coils) that may be mounted on or in catheters or other instruments and associated methods to facilitate MRI guidance of such catheters and instruments are described in U.S. Pat. Nos. 5,217,400 (Dumoulin et al.), 5,307,808 (Dumoulin et al.), 6,393,314 (Watkins et al.), 6,332,088 (Zhang et al.), 6,198,962 (Su), 6,198,962 (Su) and 6,171,240 (Young), the entire disclosure of each such United States patent being expressly incorporated herein by reference. One example of a side exit catheter operated using MRI guidance includes United States Patent Application Publication US 2003/32936 (Lederman) entire disclosure expressly incorporated herein by reference. To date, MRI guidance has not yet been used for guidance of tissue penetrating catheters from blood vessels.

In general, tissue penetrating catheters are inserted into blood vessels or other natural or man-made body lumens and advanced to a desired position. A tissue penetrator is then advanced from the catheter to a target location outside of the body lumen in which the catheter is positioned. A substance (e.g., a drug, biologic, cells, filler or other material), device (e.g., a guidewire, catheter, electrode, light guide, substance delivery implant, tool, scope, etc.) or other therapy (e.g., laser, ionizing radiation, etc.) may then be delivered by or through the tissue penetrator to the target location. In some instances the target location may be within the wall of the blood vessel or other luminal anatomical structure in which the catheter is positioned. In other instances, the target location may be another anatomical or pathological structure (e.g., a blood vessel, organ, body cavity, tumor, muscle, nerve, etc.). Examples of tissue penetrating catheter systems and their methods of use include those described in U.S. Pat. Nos. 5,830,222 (Makower), 6,068,638 (Makower), 6,159,225 (Makower), 6,190,353 (Makower, et al.), 6,283,951 (Flaherty, et al.), 6,375,615 (Flaherty, et al.), 6,508,824 (Flaherty, et al.), 6,544,230 (Flaherty, et al.), 6,579,311 (Makower), 6,602,241 (Makower, et al.), 6,655,386 (Makower, et al.), 6,660,024 (Flaherty, et al.), 6,685,648 (Flaherty, et al.), 6,709,444 (Makower), 6,726,677 (Flaherty, et al.) and 6,746,464 (Makower) the entire disclosure of each such United States patent being expressly incorporated herein by referenceImage guidance of tissue penetrating catheters can present unique challenges not associated with other types of catheters. For example, it is sometimes desirable for the operator to be provided with, not only an indication of the catheter's position within the body, but also an indication of the catheter's rotational orientation relative to the target location and/or other indication of the trajectory on which the penetrator will advance. Such indication of catheter rotational orientation and/or penetrator trajectory enables the operator to pre-orient the catheter so that, when the tissue penetrator is subsequently advanced, it will enter the target location and not some other unintended location. Thus, there remains a need in the art for the development of MRI guidable tissue penetrating catheters and related methods of use.

SUMMARY OF THE INVENTION

In accordance with the present invention there is provided a tissue penetrating catheter device that is useable in conjunction with an available MRI system such as from GE Medical Systems, Waukesha, Wis.; Siemens Medical Solutions of Siemens AG, Malvern, Pa. and Erlangen, Germany; Toshiba America Medical Systems, Inc., Tustin, Calif. as well as any other suitable MRI system. Such tissue penetrating catheter device comprises a catheter body, a tissue penetrator that is advanceable from the catheter body and at least one magnetic resonance apparatus that sends signals to the magnetic resonance imaging system. The magnetic resonance imaging system is adapted to use such signals to provide an indication of the position of the magnetic resonance apparatus and, thus, the in vivo position of the catheter body. The magnetic resonance apparatus located on or in the catheter body may comprise a magnetic resonance receiver, such as a coil or antenna (e.g., a loopless antenna). In some embodiments, the catheter device may include a magnetic resonance apparatus that indicates the path on which the penetrator will subsequently advance from the catheter body and/or the rotational orientation of the catheter body within the subject's body and/or the radial location of an opening or other discrete radial location on the catheter from which the penetrator will advance, relative to the target location. Such indicia of penetrator path, rotational orientation or radial penetrator outlet location may be used by the operator to adjust the rotational orientation of the catheter body prior to advancement of the penetrator to ensure, or at least increase the likelihood, that the penetrator will advance to the target location rather than some other location. In some embodiments, the tissue penetrator may be an elongate penetrator member (e.g., a needle) having a hollow lumen through which a substance, article or device may be introduced.

Further in accordance with the invention, there are provided methods for creating a penetration tract from a location within a body lumen (e.g., a blood vessel lumen or other natural or man-made anatomical passageway) to a location outside of that body lumen. Such method generally comprises the steps of (A) providing a tissue penetrating catheter device that comprises i) a catheter body having a distal end, ii) a tissue penetrator that is advanceable from the catheter body and iii) at least one magnetic resonance apparatus that sends signals to a magnetic resonance imaging system adapted to use said signals to provide an indication of the current position of said at least one magnetic resonance apparatus; (B) inserting the tissue penetrating catheter into the subject's body; (C) causing a magnetic resonance imaging system to receive signals from said at least one magnetic resonance apparatus and to provide, in response to the received signals, an indication of the current position of the at least one magnetic resonance apparatus within the subject's body; (D) using the indication of the current position of the at least one magnetic resonance apparatus within the subject's body to guide the tissue penetrating catheter to a position within said body lumen near the target location, and (E) advancing the tissue penetrator from the tissue penetrating catheter to the target location. In some embodiments, the tissue penetrating catheter device will include a magnetic resonance apparatus that provides indicia of the path on which the penetrator will subsequently advance from the catheter body and/or the rotational orientation of the catheter body within the subject's body and/or the radial location of an opening or other discrete radial location on the catheter from which the penetrator will advance, relative to the target location, and the operator may use such indicia to adjust the rotational orientation of the catheter within the subject's body as necessary to ensure, or at least increase the likelihood, that the penetrator will advance in Step E to the intended target location rather than some other location. In some embodiments, the tissue penetrator may be an elongate penetrator member (e.g., a needle) having a hollow lumen through which a substance, article or device may be introduced and the method may further include the step of introducing a substance (e.g., a therapeutic or diagnostic substance), article (e.g., an implant) or device (e.g., a guidewire, catheter, apparatus, etc.) through the penetrator lumen.

Further aspects, details and embodiments of the present invention will be understood by those of skill in the art upon reading the following detailed description of the invention and the accompanying drawings.

BRIEF DESCRIPTION OF THE DRAWINGS

FIG. 1A is an enlarged side view of the distal end of the tissue penetrating catheter device shown in FIG. 1.

FIG. 1B is a cross sectional view through line 1B-1B of FIG. 1A.

The Figures are not necessarily to scale.

DETAILED DESCRIPTION

The following detailed description, the accompanying drawings are intended to describe some, but not necessarily all, examples or embodiments of the invention. The contents of this detailed description and accompanying drawings do not limit the scope of the invention in any way.

Figure 1:
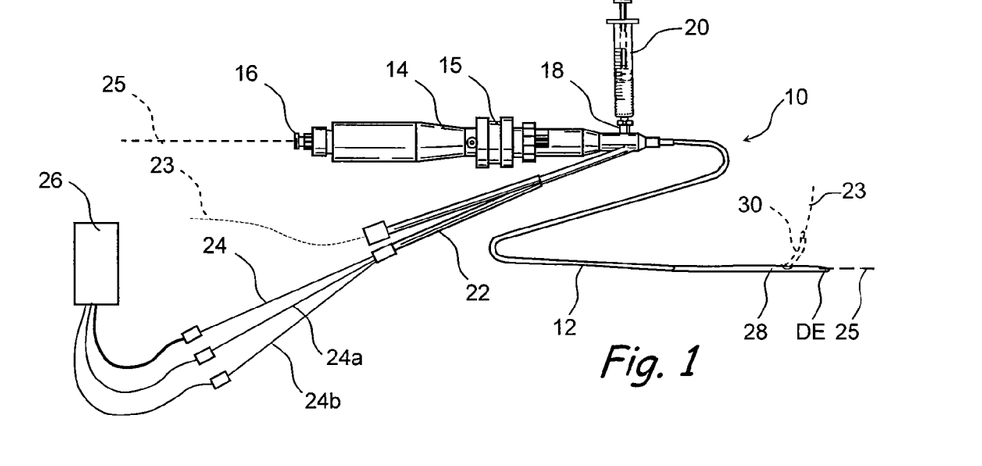
FIG. 1 is a side view of one embodiment of an MRI guidable tissue penetrating catheter device of the present invention.
Figure 1C:
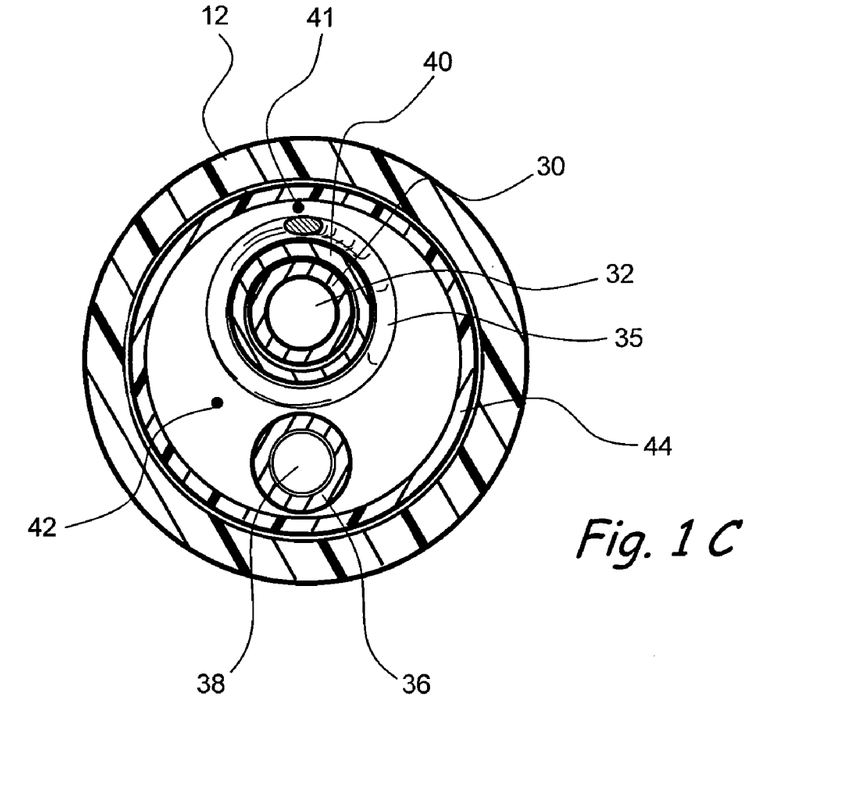
FIG. 1C is a cross sectional view through line 1C-1C of FIG. 1A.
Figure 1D:
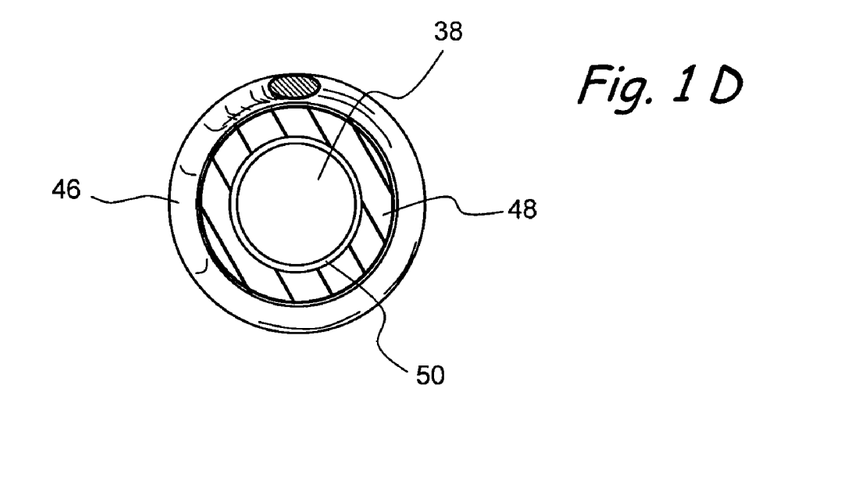
FIG. 1D is a cross sectional view through line 1D-1D of FIG. 1A.

FIGS. 1-1D show one of many possible examples of an MRI guidable tissue penetrating catheter device 10 of the present invention. This catheter device 10 is useable in conjunction with a separate MRI system 26 that is programmed to receive and process signals from MRI apparatus 34, 35, 46 mounted at different positions on the catheter device 10. In the preferred embodiment shown, each MRI apparatus 34, 35, 46 comprises a coil. Each coil may be made of a conductive material and is shielded along the majority of its length to inhibit interference as is well known in the art. Although in the preferred embodiment coils are provided, it should be understood that other devices to create an image in an MRI image may also be used. Although an object which is literally a coil is used in the preferred embodiment, the invention may be practiced using any other suitable receiving structure, including objects which may not be literally a coil. Also, it should be noted that the coil does not need to be coaxial with the member it is intended to track. It can be a planar coil that is adjacent to or touching or embedded within the member being tracked. Each coil is connected to the proximal end of the catheter device 10 to a proximal connector 24a, 24b and/or 24c. Each proximal connector is, in turn, connected to the MRI system 26 through an impedance matching circuit as is well known in the art such that signals from the MRI apparatus 34, 35, and/or 46 (e.g., the coils) are received by the MRI system 26. The MRI system 26 is programmed to display, in response to such signals received from MRI apparatus 34, 35, and/or 46, the positions of such MRI apparatus 34, 35, and/or 46 relative to anatomical structures within the subject's body in a so-called real time manner. In an alternative embodiment, the MRI apparatus may be superimposed into a prior MRI imaging scan stored in memory using known techniques. In a further embodiment immobile landmarks (such as a bony prominences) may be used as internal fiducials to superimpose historical with current or real-time images for such tracking. This may be accomplished using image-rendering software employing known techniques.

In general, this example of the catheter device 10 comprises an elongate, flexible catheter body 12 and a handpiece 14. A side port 41 is formed in the sidewall of the catheter body, as seen in FIG. 1A. A tissue penetrator 30 is moveable between a retracted position, where at least the distal portion of the penetrator 30 is within a curved tubular penetrator housing 40 as seen in FIG. 1C, and an extended position wherein the penetrator 30 extends out of side port 41, as shown in FIG. 1A.

It will be appreciated that the penetrator 30 may comprise any member (e.g., a probe or needle), apparatus (e.g., an electrosurgical probe) or energy form (e.g., laser beam) capable of penetrating tissue. In the particular embodiment shown in the drawings, the penetrator 30 comprises a curved needle having a hollow lumen 32 and an open distal end. A proximal side arm 27 is connected to the proximal end of the penetrator lumen 32 such that a substance, article or device may be delivered through the proximal side arm 23 and through the lumen 32 of the penetration member 30. In the particular example shown in FIGS. 1 and 1A, a non-ferrous guidewire 23 (e.g., a 0.014-inch nickel titanium alloy guidewire available Terumo Medical Corporation, Somerset, N.J.) is advanced through proximal side arm, 27, through the lumen 32 of the penetrator 30 and out of the distal end of the penetrator 30. Some non-limiting examples of other devices, articles and substances that may be delivered through the penetrator lumen 32 are described below.

With reference to FIG. 1, the handpiece 14 comprises a penetrator advancement/retraction knob 15 which may be pushed in the distal direction to advance the penetrator 30 from its retracted position to its extended position and pulled in the proximal direction to retract the penetrator from its extended position to its retracted position. An adjustable stop member 17 limits the extent of distal advancement of the penetrator advancement/retraction knob 15, thereby controlling the length from the side port 28 to the distal tip of the penetrator 30 when the penetrator 30 is fully extended.

A tube 36 extends from a proximal port 16 on the handpiece 14 through the catheter body. A tapered distal tip member 39 having a lumen 38 is mounted on the distal end of the catheter body 12. The distal tip member lumen 38 is continuous with the lumen 38 of tube 36, such that a continuous lumen extends from proximal port 16 though the open distal end of distal tip member 39. A guidewire 25 may pass through this lumen 38, 38 (tip) for over-the-wire advancement of the catheter device 10. It will be appreciated that, in some alternative embodiments, the lumen 38 may terminate proximally in a side opening in the catheter body 12, thereby providing a rapid exchange type guidewire lumen.

In the embodiment shown in FIGS. 1-1D, an infusion port 18 is optionally formed on the handpiece 14 in communication with lumen 38 such that an infusion apparatus 20 (e.g., a syringe, intravenous tube, pump, injector, etc.) may be used to infuse fluid (e.g., saline solution, radiographic contrast medium, etc.) through lumen 38, 38 (tip) and out of the open distal end of the tip member 46. A valve (e.g., a Tuoghy Borst valve) may be provided on proximal port 16 to secure a guidewire 25 when desired and/or to form a fluid tight seat at proximal port 16 when fluid is being infused through infusion port 18.

The catheter device 10 shown in this example incorporates three (3) MRI apparatus 34, 35, 46 (e.g., the coils), each of which indicates the in vivo position and/or rotational orientation of a different portion of the catheter device 10.

A first MRI apparatus 34 comprises an MRI receiver coil wound about the penetrator 30 at a location near its distal end, such that first MRI apparatus 34 will indicate the position of the distal portion of the penetrator 30 on the MRI system display. This enables the operator to determine, from an MRI display, when the distal end of the penetrator has entered an intended target location.

Second MRI apparatus 35 comprises an MRI receiving coil wound about the curved needle housing 40, such that second MRI apparatus 35 will indicate on the MRI display the location of the needle housing 40. Additionally, by providing an image of the curvature of the needle housing, second MRI apparatus 35 will indicate the rotational orientation of the catheter body 12 and, thus, the path or trajectory on which the penetrator 30 will subsequently advance.

Third MRI apparatus 46 comprises an MRI receiving coil wound about the distal tip member 39, near the distal end DE of the catheter body. This enables the operator to determine, from an MRI display, the real time in vivo location of the distal end DE of the catheter device 10.

Figure 2A:
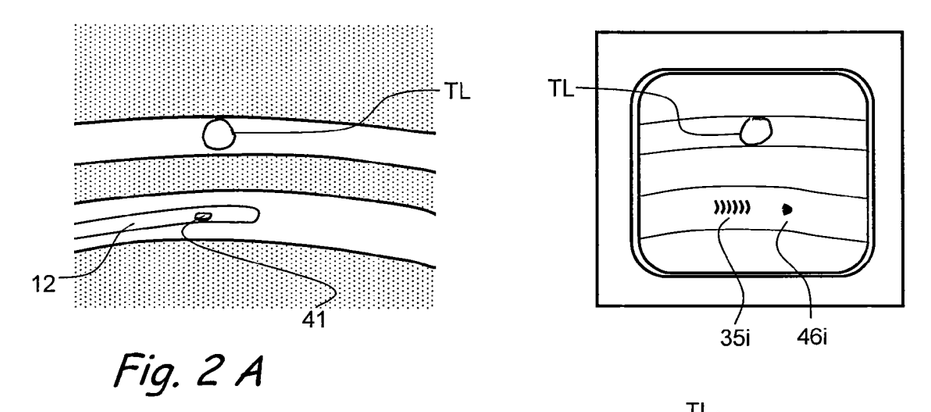
FIGS. 2A through 2C show steps in a method for using the MRI guidable tissue penetrating catheter device of FIG. 1 to form a penetration tract from a location within the lumen of one blood vessel to a target location within the lumen of another blood vessel.
Figure 2B:
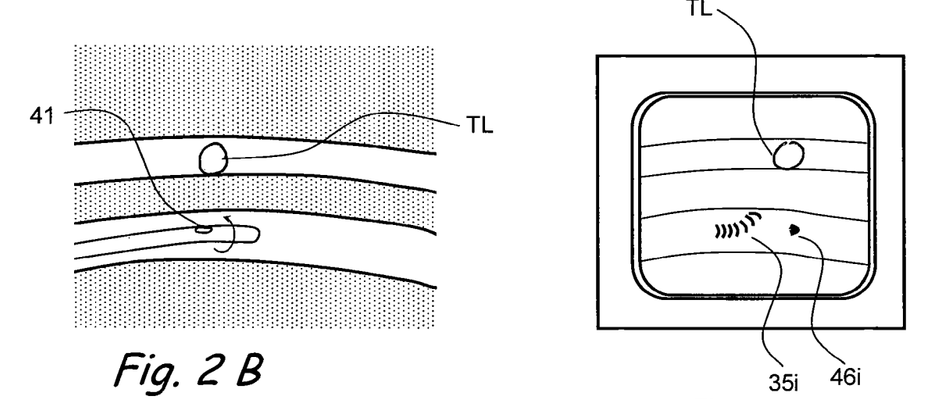
Figure 2C:
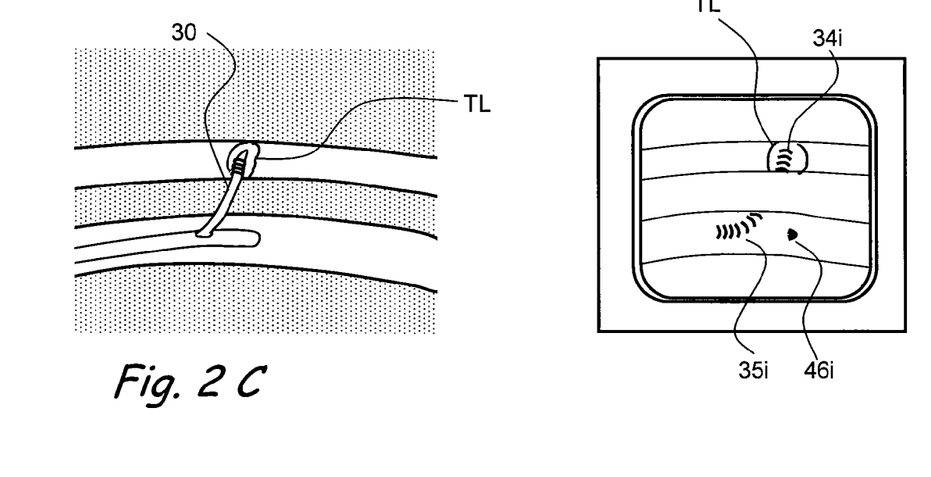

FIGS. 2A-2C show an example of a method by which the catheter device 10 may be used. Each of FIGS. 2A-2C shows a diagram of the catheter body 12 positioned within a body lumen BL (e.g., a blood vessel) on the left and a corresponding MRI system display on the right.

In FIG. 2A, the catheter body 12 is positioned within the body lumen BL and rotationally orientated such that the side opening 41 from which the penetrator 30 will emerge is rotated approximately 90 degrees away from the target location TL. Accordingly, the MRI system display in FIG. 2A shows the second MRI apparatus image 35$i$ as a straight line adjacent to the target location TL and aligned directly behind the third MRI apparatus image 46$i$ indicating the position of the distal end of the catheter body 12 within the body lumen BL. From this image, the operator can see that the longitudinal position of the catheter body 12 is generally suitable but the rotational orientation of the catheter body is off by approximately 90 degrees. Thus, if the penetrator 30 were to be advanced while the catheter body 12 is in its current rotational orientation, the penetrator 30 would not enter the target location TL but rather would penetrate into other tissue adjacent to the body lumen BL, potentially causing unwanted trauma or damage.

In FIG. 2B, the operator rotates the catheter body 12 until the third MRI apparatus image 46$i$ on the MRI system display shows the curvature of the penetrator housing 40 pointing directly toward the target location TL. This indicates to the operator that the catheter body 12 is properly positioned and oriented for subsequent advancement of the penetrator 30 to the target location TL.

In FIG. 2C the penetrator 30 is advanced out of opening 41, through the wall of the body lumen BL in which the catheter body 12 is positioned and into the target location TL. The first MRI apparatus image 34$i$ shown on the MRI system display indicates to the operator that the distal end of the penetrator 30 has entered the target location, as desired. At this time, any desired device, article or substance may be delivered though the penetrator lumen 32 to the target location TL.

It should be noted that different MRI apparatus 34, 35, 46 (e.g., the coils) can be linked to different channels in the MRI system, such that each coil (and thus the device region it is tracking) can be depicted on the MRI image in a different color. Such an embodiment may permit navigation more user-friendly.

One particular advantage of the present invention is that it may allow the use of an MRI for delivery materials to areas requiring the discrimination of an MRI to identify (e.g. infarcted or ischemic tissue, tumor, etc.). In FIG. 2A-c such a region was depicted as target location TL. Because an MRI illustrates and displays well areas of infarction or ischemia, the present invention is believed to be particularly useful to visualize and locate exactly where an area of infarction or ischemia is and thus better able to deliver drugs, etc right into such an area. Moreover, while this benefit is depicted as permitting discerning non-viable from viable myocardium, it may also be used to advantage for delivering a therapy-containing catheter to any other type of damaged or non-viable tissue (nerve, muscle, liver, spleen, pancreas, kidney, brain, etc.).

It is to be appreciated that the catheter device 10 and method may be used for many different purposes wherein it is desired to penetrate from a location within a body lumen to some target location outside of that body lumen. In some instances, the target location may be in the wall of a vessel in which the catheter body 12 is positioned. For example, the wall of a blood vessel is made up of several layers (e.g., tunica intima, tunica media and tunica adventitia or outer coat) and the penetrator 30 may be advanced from the lumen of the blood vessel to a location within the blood vessel wall (e.g., into the adventitia or outer coat of the blood vessel. This technique may facilitate delivery of therapeutic substances into the luminal vessel wall. For example, this technique may be used for injection of drugs into an artery wall to deter restenosis of the artery following an angioplasty procedure.

In other instances, the target location may be outside of the wall of the luminal anatomical structure in which the catheter body 12 is positioned and the penetrator 30 may be advanced all the way through the luminal wall to the desired target location. For example, the catheter body 12 may be positioned within the lumen of one blood vessel and the penetrator 30 may be advanced to a target location within the lumen of another blood vessel. Such vessel-to-vessel penetration may be utilized to create, or to facilitate the creation of, a passageway or fistula between two blood vessels. Or, as a further example, the target location may be a natural or man made cavity or structure located adjacent to or a spaced distance away from the body lumen in which the catheter body 12 is positioned. Examples of such possible target locations include organs, tumors, body cavities, previously implanted devices such as substance reservoirs or drug eluting devices, etc. Targets may also include different layers within an organ or tissue such as the potential space between two tissue layers. For example, the target may be the sub-endocardium or the sub-epicardium.

Also, in some instances, the penetration catheter 10 may be inserted into a man made passage such as a guidewire tract or neo-lumen created in the wall of a blood vessel past an occlusive lesion (e.g., a chronic total occlusion) and the penetrator 30 may then be advanced to a target location within the true lumen of that blood vessel downstream of the obstruction. In such procedures, if the penetrator 30 has a lumen 32, a guidewire may be advanced through the penetrator lumen 32 into the true lumen of the blood vessel downstream of the obstruction. Thereafter, the penetrator 30 may be retracted and the penetrating catheter device 10 removed, leaving the guidewire in place. A stent may then be delivered over that guidewire and used to stent the man made guidewire tract (e.g., "neo-lumen) thereby providing a bypass conduit for blood flow around the obstructive lesion.

In applications of the invention where a flowable substance is to be delivered via the penetrator 30 to the target location, it will be appreciated that the substance may in some cases be delivered directly though a lumen 32 formed in the penetrator 30 and in other cases a separate catheter may be advanced through the lumen 32 of the penetrator 30 and the flowable substance may then be delivered through that separate catheter. Examples of the types of substances that may be delivered include but are not limited to: contrast agents or other agents that provide an enhanced image of the target site, traceable substances that may be used to determine the rate at which the substance distributes away from or is otherwise inactivated at the target site or other pharmacokinetic or biodistributive parameters or variables, drugs, proteins, cells (e.g., stem cells, nerve cells, progenitor cells, myoblasts, myocytes, secretory cells, pancreatic islet cells, dopamine secreting cells, endothelial cells, hepatocytes, cloned cells, cells grown in cell culture, genetically modified cells, and combinations thereof), angiogenic substances (e.g., vascular endothelial growth factor (VEGF), fibroblast growth factors (FGF), epidermal growth factor (EGF), platelet-derived growth factor (PDGF), hepatocyte growth factor (HGF) or scatter factor, heparin combined with an adenosine receptor agonist, nerve cell growth factor (NGF), and combinations thereof), other agents that increase vascularity of an ischemic target site, myogenic substances, neurogenic substances, genes, gene therapy compositions, genetic material in combination vectors (e.g., viruses), stem cells of a type that will mature in situ into a type of cell that is currently deficient, substances that promote the growth of myocytes in tissue that is necrotic or characterized by a lack of living myocytes, secretory cells that secrete a substance (e.g., dopamine, insulin, a particular neurotransmitter) that is deficient, tep F comprises insulin secreting cells, glial cell line-derived neurotropic factor (GDNF), nerve growth factor, neuro-immunophilin ligand, poly ADP-Ribose polymerase, and combinations thereof.

In applications of the invention where an article is to be delivered to the target site, it will be appreciated that in some cases such article may be introduced directly through the lumen 32 of the penetrator 30 and in other cases a tube or other delivery device may be advanced through the penetrator 30 and used to deliver the desire article. Examples of the types of articles that may be delivered include but are not limited to; substance eluting implants, radioactive implants, embolic members, markers, as well as radiopaque markers, etc.

In applications of the invention where a device is to be delivered to the target site, it will be appreciated that in some cases such device may be introduced directly through the lumen 32 of the penetrator 30 and in other cases a delivery device (e.g., a guidewire or catheter) may initially be advanced through the lumen 32 of the penetrator 30 and second device (e.g., a working device) may then be delivered to the target location by way of that delivery device. Examples of the types of articles that may be delivered include but are not limited to; catheters, cannulae, guidewires, wires, electrodes, sensors, microreservoirs, implantable devices, substance eluting or delivering devices, etc.

It is to be further appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. Also, where the steps of a method or process are described, listed or claimed in a particular order, such steps may be performed in any other order unless to do so would render the embodiment or example not novel, obvious to a person of ordinary skill in the relevant art or unsuitable for its intended use. All reasonable additions, deletions, modifications and alterations are to be considered equivalents of the described examples and embodiments and are to be included within the scope of the following claims.

What is claimed is:

1. A tissue penetrating catheter device useable with a magnetic resonance imaging system, said device comprising:
a catheter body having a distal end;
a tissue penetrator that is advanceable from the catheter body; and
at least one magnetic resonance apparatus that sends signals to a magnetic resonance imaging system adapted to use said signals to provide an indication of the position of said at least one magnetic resonance apparatus;
wherein said at least one magnetic resonance apparatus comprises a first magnetic resonance apparatus located at a first location on or in the catheter body at or near the distal end of the catheter body, a second magnetic resonance apparatus located at a second location situated on or in the penetrator and a third magnetic resonance apparatus located at a third location on or in the catheter body at or near a location where the tissue penetrator advances out of the catheter body.

2. A device according to claim 1 wherein said at least one magnetic resonance apparatus comprises at least one coil.

3. A device according to claim 1 wherein said at least one magnetic resonance apparatus comprises at least one magnetic resonance receiver.

4. A device according to claim 1 wherein a magnetic resonance apparatus is located on or in the catheter body.

5. A device according to claim 1 wherein a magnetic resonance apparatus is located on or in the penetrator.

6. A device according to claim 1 wherein a first magnetic resonance apparatus is located on or in the catheter body and a second magnetic resonance apparatus is located on or in the penetrator.

7. A device according to claim 1 wherein the tissue penetrator comprises an elongate member having a lumen.

8. A device according to claim 1 wherein the tissue penetrator comprises a needle.

9. A device according to claim 1 wherein said at least one magnetic resonance apparatus comprises at least one antenna.

10. A device according to claim 4 wherein said at least one magnetic resonance apparatus comprises at least one loopless antenna.

11. A device according to claim 1 wherein the tissue penetrator comprises an elongate penetration member and wherein the device further comprises a penetrator housing within which at least a portion of the elongate penetration member resides when in its retracted position.

12. A device according to claim 11 wherein a first magnetic resonance apparatus is located at or near the distal end of the catheter body, a second magnetic resonance apparatus is located on or in the penetrator member and a third magnetic resonance apparatus is located on, in or adjacent to the penetrator housing.

13. A device according to claim 11 wherein a magnetic resonance apparatus is located on, in or adjacent to the penetrator housing.

14. A device according to claim 13 wherein the penetrator housing comprises a tubular penetrator housing and wherein a magnetic resonance apparatus comprises a coil that substantially surrounds the tubular penetrator housing.

15. A device according to either of claim 11 or 13 wherein the penetrator exits from a side opening in the catheter body and the penetrator housing is curved in the direction of sad side opening.

16. A device according to claim 15 wherein a magnetic resonance apparatus is positioned on, in or adjacent to the curved penetrator housing such that it provides an image of the penetrator housing.

17. A device according to claim 16 wherein the penetrator housing is shaped such that a portion of the penetrator housing is in alignment with the trajectory on which the penetrator will advance from the catheter body, the image of the penetrator housing being thereby generally useable as an indication of the trajectory on which the penetrator will advance from the catheter body.

18. A device according to claim 1 wherein the tissue penetrator has a lumen through which a substance, article or device may be delivered.

19. A system comprising a device according to claim 18 in combination with substance delivery apparatus useable to deliver a substance through the lumen of the tissue penetrator.

20. A system comprising a device according to claim 18 in combination with a catheter that is advanceable through the lumen of the tissue penetrator.

21. A system according to claim 20 wherein the catheter that is advanceable through the lumen of the tissue penetrator comprises a microcatheter.

22. A system comprising a device according to claim 18 in combination with a device that is advanceable through the lumen of the tissue penetrator.

23. A system according to claim 22 wherein the device that is advanceable through the lumen of the tissue penetrator comprises a guidewire.

24. A system according to claim 1 in combination with a magnetic resonance system that is programmed to receive signals from the at least one magnetic resonance apparatus and to display the location of the at least one magnetic resonance apparatus in response to said signals.

25. A system according to claim 24 wherein the magnetic resonance system displays the location of the at least one magnetic resonance apparatus in relation to images of anatomical structures located near the current position of the at least one magnetic resonance apparatus.

26. A system according to claim 24 wherein the location of the at least one magnetic resonance apparatus is superimposed on an anatomical image.

27. A system according to claim 24 wherein the tissue penetrating catheter device includes a plurality of magnetic resonance apparatus and wherein the magnetic resonance system displays a different indicator for the position of each magnetic resonance apparatus.

28. A system according to claim 27 wherein the magnetic resonance system displays a different colored indicator for the location of each magnetic resonance apparatus.

29. A system according to claim 24 wherein the magnetic resonance system receives signals from the at least one magnetic resonance apparatus defining the rotational orientation of the tissue penetrating catheter device and in response to said signals displays an indication of the rotational orientation of the tissue penetrating catheter device.

* * * * *

UNITED STATES PATENT AND TRADEMARK OFFICE
CERTIFICATE OF CORRECTION

PATENT NO. : 8,214,015 B2
APPLICATION NO. : 11/279773
DATED : July 3, 2012
INVENTOR(S) : Macaulay et al.

Page 1 of 1

It is certified that error appears in the above-identified patent and that said Letters Patent is hereby corrected as shown below:

In the Claims

Column 9, line 25

"...according to claim 4..."

should be changed to

--according to claim 9--

Column 9, line 48

"...direction of sad side opening..."

should be changed to

--direction of said side opening--

Column 10, line 35

"...according to claim 24..."

should be changed to

--according to claim 25--

Signed and Sealed this
Twenty-ninth Day of October, 2013

Teresa Stanek Rea
*Deputy Director of the United States Patent and Trademark Office*